US010786567B2

(12) United States Patent
Li et al.

(10) Patent No.: US 10,786,567 B2
(45) Date of Patent: Sep. 29, 2020

(54) STABLE ANTI-PD-1 ANTIBODY PHARMACEUTICAL PREPARATION AND APPLICATION THEREOF IN MEDICINE

(71) Applicants: Suzhou Suncadia Biopharmaceuticals Co., Ltd., Suzhou, Jiangsu (CN); Jiangsu Hengrui Medicine Co., Ltd., Lianyungang, Jiangsu (CN); Shanghai Hengrui Pharmaceutical Co., Ltd., Shanghai (CN)

(72) Inventors: Jie Li, Shanghai (CN); Zhen Yan, Shanghai (CN); Pingping Wang, Shanghai (CN); Yan Fang, Shanghai (CN); Weikang Tao, Shanghai (CN); Lianshan Zhang, Shanghai (CN); Piaoyang Sun, Jiangsu (CN)

(73) Assignees: Suzhou Suncediabiopharmaeuticals Co., Ltd., Suzhou, Jiangsu (CN); Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 87 days.

(21) Appl. No.: 15/761,552

(22) PCT Filed: Sep. 14, 2016

(86) PCT No.: PCT/CN2016/098982
§ 371 (c)(1),
(2) Date: Mar. 20, 2018

(87) PCT Pub. No.: WO2017/054646
PCT Pub. Date: Apr. 6, 2017

(65) Prior Publication Data
US 2018/0339045 A1 Nov. 29, 2018

(30) Foreign Application Priority Data

Sep. 28, 2015 (CN) .......................... 2015 1 0629020

(51) Int. Cl.
| A61K 39/395 | (2006.01) |
| A61K 47/02 | (2006.01) |
| A61K 47/26 | (2006.01) |
| A61K 47/12 | (2006.01) |
| A61K 9/00 | (2006.01) |
| A61K 9/08 | (2006.01) |
| A61K 9/19 | (2006.01) |
| C07K 16/28 | (2006.01) |

(52) U.S. Cl.
CPC ...... *A61K 39/39591* (2013.01); *A61K 9/0019* (2013.01); *A61K 9/08* (2013.01); *A61K 9/19* (2013.01); *A61K 39/395* (2013.01); *A61K 47/02* (2013.01); *A61K 47/12* (2013.01); *A61K 47/26* (2013.01); *C07K 16/2818* (2013.01); *C07K 2317/76* (2013.01)

(58) Field of Classification Search
None
See application file for complete search history.

(56) References Cited

U.S. PATENT DOCUMENTS

| 7,740,842 | B2 * | 6/2010 | Arvinte | ............... A61K 9/0019 424/130.1 |
| 2016/0376367 | A1 * | 12/2016 | Yuan | ............... C07K 16/2818 424/139.1 |

FOREIGN PATENT DOCUMENTS

| CN | 103429264 A | 12/2013 |
| WO | 2015085847 A1 | 6/2015 |
| WO | 2017054646 A1 | 4/2017 |

OTHER PUBLICATIONS

Cleland et al, "The Development of Stable Protein Formulations: A close Look at Protein Aggregation, Deamidation, and Oxidation," Crit Rev Ther Drug Carrier Syst, vol. 10, Iss. 4, pp. 307-377 (1993).
Wang, Wei, "Instability, stabilization, and formulation of liquid protein pharmaceuticals," Int J. Pharm, vol. 20, pp. 129-188 (1999).
Wang, Wei, "Lyophilization and development of solid protein pharmaceuticals," Int J. Pharm, vol. 10, pp. 1-60 (2000).
Chi et al, "Physical Stability of Proteins in Aqueous Solution: Mechanism and Driving Forces in Nonnative Protein Aggregation," Pharm Res. vol. 20, No. 9, pp. 1325-1336 (2003).
Written Opinion dated Dec. 20, 2016 in Int'l Application No. PCT/CN2016/098983.

* cited by examiner

*Primary Examiner* — Yunsoo Kim
(74) *Attorney, Agent, or Firm* — Ice Miller LLP (57) ABSTRACT

A stable anti-PD-1 antibody pharmaceutical preparation and an application thereof in a medicine. The anti-PD-1 antibody pharmaceutical preparation comprises an anti-PD-1 antibody, a buffer, and can further comprise at least one type of stabilizer, and optionally can further comprise a surfactant. The anti-PD-1 antibody pharmaceutical preparation of the present invention can effectively suppress antibody aggregation and deamidation, thereby preventing degradation of an antibody product, resulting in a stable injectable pharmaceutical preparation.

18 Claims, 1 Drawing Sheet
Specification includes a Sequence Listing.

STABLE ANTI-PD-1 ANTIBODY PHARMACEUTICAL PREPARATION AND APPLICATION THEREOF IN MEDICINE

CROSS-REFERENCE TO RELATED APPLICATION

This application is a Section 371 of International Application No. PCT/CN2016/098982, filed Sep. 14, 2016, which was published in the Chinese language on Apr. 6, 2017, under International Publication No. WO 2017/054646 A1, which claims priority under 35 U.S.C. § 119(b) to Chinese Application No. 201510629020.X, filed Sep. 28, 2015, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "sequence_listing" and a creation date of Mar. 12, 2018, and having a size of 7.2 kb. The sequence listing submitted via EFS-Web is part of the specification and is herein incorporated by reference in its entirety.

FIELD OF THE INVENTION

The present invention relates to a pharmaceutical formulation comprising an anti-PD-1 antibody or antigen-binding fragment thereof, a manufacture process of the formulation and the use of the formulation.

BACKGROUND OF THE INVENTION

There is an extremely complex relationship between tumor immune escape mechanism and body's immune response to tumors. For immunotherapy, during the early stage of cancer, tumor-specific killer T cells have their biological activity, however, they lose the tumor-specific killing function in the late stage with the tumor growth. In order to enhance the patient's own immune system response to tumor to the maximum, the key of tumor immunotherapy is not only to activate the existing immune system response, but also to maintain the duration and intensity of the immune system response.

Programmed death-1 (PD-1), discovered in 1992, is a protein receptor expressed on T cell surface, and is involved in cell apoptosis. PD-1 belongs to CD28 family, exhibits 23% amino acid homology with cytotoxic T lymphocyte antigen 4 (CTLA-4). However, unlike CTLA4, PD-1 is mainly expressed in activated T cells, B cells and myeloid cells. PD-1 has two ligands, PD-L1 and PD-L2 respectively. New studies have detected high level of expression of PD-L1 protein in human tumor tissues such as breast cancer, lung cancer, stomach cancer, intestinal cancer, kidney cancer, and melanoma, and the expression level of PD-L1 is closely related to patient's clinical response and prognosis. Since PD-L1 inhibits T cell proliferation in the second signaling pathway, PD-L1 becomes a very promising new target in field of cancer immunotherapy via blocking the binding of PD-1 to PD-L1.

WO2015/085847 discloses a novel class of anti-PD-1 antibodies, which are characterized by high affinity and long half-life, and are expected to have a better therapeutic effect on the above-mentioned diseases. However, these new anti-PD-1 antibodies can be extremely unstable, and difficult to be formulated into a clinically feasible preparation. There is no detailed description on how these new anti-PD-1 antibodies are formulated in the PCT application. Therefore, it is necessary to carry out in-depth study of these antibodies in order to obtain a formulation for stable and convenient clinical use.

SUMMARY OF THE INVENTION

The aim of the present invention is to provide a stable anti-PD-1 antibody formulation.

The stable pharmaceutical formulation of the present invention contains an anti-PD-1 antibody or an antigen-binding fragment thereof and a buffer. The pharmaceutical formulation further contains at least one stabilizer, and optionally a surfactant.

In a pharmaceutical formulation of the present invention, the anti-PD-1 antibody or antigen binding fragment thereof comprises any one or more CDR region sequences selected from the following sequences and amino acid sequences having at least 85% identity to the following sequences:

antibody heavy chain variable region HCDR sequences: SEQ ID NO: 1, SEQ ID NO: 2, and SEQ ID NO: 3; and
antibody light chain variable region LCDR sequences: SEQ ID NO: 4, SEQ ID NO: 5, and SEQ ID NO: 6.

The amino acid sequences are shown in the following table:

| | | Anti-PD-1 antibody | |
|---|---|---|---|
| | Domain | Sequence | SEQ ID NO |
| VH | HCDR1 | SYMMS | 1 |
| | HCDR2 | TISGGGANTYYPDSVKG | 2 |
| | HCDR3 | QLYYFDY | 3 |
| VL | LCDR1 | LASQTIGTWLT | 4 |
| | LCDR2 | TATSLAD | 5 |
| | LCDR3 | QQVYSIPWT | 6 |

The sequence homology can be derived from conventional methods for improving the affinity or immunogenicity or stability of the antibody or other conventional physical and chemical properties or biological activity.

A further preferred anti-PD-1 antibody comprises a heavy chain having the amino acid sequence of SEQ ID NO: 7 and a light chain having the amino acid sequence of SEQ ID NO: 8.

SEQ ID NO: 7
EVQLVESGGGLVQPGGSLRLSCAASGFTFSSYMMSWVRQAPGKGLEWVAT

ISGGGANTYYPDSVKGRFTISRDNAKNSLYLQMNSLRAEDTAVYYCARQL

YYFDYWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

-continued

QEEMTKNQVSLTCLVKGFYPSDIAVEWESNGQPENNYKTTPPVLDSGSF

FLYSRLTVDKSRWQEGNVFSCSVMHEALHNHYTQKSLSLSLGK,

SEQ ID NO: 8
DIQMTQSPSSLSASVGDRVTITCLASQTIGTWLTWYQQKPGKAPKLLIYT

ATSLADGVPSRFSGSGSGTDFTLTISSLQPEDFATYYCQQVYSIPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

The concentration of the anti-PD-1 antibody in a pharmaceutical formulation of the present invention can be 1 mg/ml to 60 mg/ml, preferably 20-50 mg/ml, more preferably 35-45 mg/ml, most preferably 40 mg/ml.

The buffer in a pharmaceutical formulation of the present invention can be one or more selected from the group consisting of an acetate buffer, a citrate buffer, a succinate buffer, and a phosphate buffer, wherein the phosphate is selected from the group consisting of sodium dihydrogen phosphate and potassium dihydrogen phosphate. A preferred buffer is an acetate buffer. The amount of the buffer in the pharmaceutical formulation is not particularly limited in embodiments of the present invention, which can be, for example, 1 to 50 mM, preferably 2 to 20 mM, more preferably 5 to 15 mM, and most preferably 10 mM.

The pH of a formulation of the present invention can range from 4.5 to 6.0, preferably from 4.8 to 5.6, most preferably pH 5.2.

The at least one stabilizer in a pharmaceutical formulation of the present invention can be a saccharide or an amino acid. Preferably, the saccharide is a disaccharide selected from the group consisting of sucrose, lactose, trehalose and maltose, more preferably trehalose, most preferably α,α-trehalose dihydrate. The amount of the disaccharide in the pharmaceutical formulation is not particularly limited in embodiments of the present invention, which can be, for example, 30 to 120 mg/ml, preferably 60 to 100 mg/ml, more preferably 85 to 95 mg/ml, most preferably 90 mg/ml.

The surfactant in a pharmaceutical formulation of the present invention can be selected from the group consisting of polyoxyethylene hydrogenated castor oil, glycerol fatty acid esters, and polyoxyethylene sorbitan fatty acid esters. The polyoxyethylene sorbitan fatty acid ester can be selected from the group consisting of polysorbate 20, 40, 60 and 80. The amount of the surfactant in the pharmaceutical formulation is not particularly limited in embodiments of the present invention, which can be for example, 0.01 to 1 mg/ml, preferably 0.05 to 0.5 mg/ml, more preferably 0.1 to 0.4 mg/ml, most preferably 0.2 mg/ml.

A stable pharmaceutical formulation of the present invention can be an injectable pharmaceutical formulation.

In one embodiment of the present invention, a stable pharmaceutical formulation consists of an anti-PD-1 antibody, a buffer, a disaccharide and a surfactant, optionally including water.

In one embodiment of the present invention, a stable pharmaceutical formulation comprises:

In one embodiment of the present invention, a stable pharmaceutical formulation comprises:

an anti-PD-1 antibody, wherein the humanized antibody comprises a heavy chain having the amino acid sequence of SEQ ID NO: 7 and a light chain having the amino acid sequence of SEQ ID: 8; and (i) 90 mg/ml α,α-trehalose dihydrate, and 10 mM acetate buffer at pH 5.2; or
(ii) 90 mg/ml α,α-trehalose dihydrate, 0.2 mg/ml polysorbate 20, and 10 mM acetate buffer at pH 5.2; or
(iii) 90 mg/ml α,α-trehalose dihydrate, 0.2 mg/ml polysorbate 20, and 20 mM acetate buffer at pH 5.4; or
(iv) 60 mg/ml α,α-trehalose dihydrate, 0.4 mg/ml polysorbate 20, and 20 mM acetate buffer at pH 5.0; or
(v) 60 mg/ml α,α-trehalose dihydrate, 0.1 mg/ml polysorbate 20, and 20 mM acetate buffer at pH 5.2; or
(vi) 60 mg/ml α,α-trehalose dihydrate, 0.2 mg/ml polysorbate 20, and 10 mM acetate buffer at pH 5.2; or
(vii) 30 mg/ml α,α-trehalose dihydrate, 0.4 mg/ml polysorbate 20, and 10 mM acetate buffer at pH 4.8; or
(viii) 30 mg/ml α,α-trehalose dihydrate, 0.2 mg/ml polysorbate 20, and 30 mM acetate buffer at pH 5.2; or
(ix) 30 mg/ml α,α-trehalose dihydrate, 0.4 mg/ml polysorbate 20, and 10 mM acetate buffer at pH 5.6.

An injectable pharmaceutical formulation can be in the form of an injection solution or further prepared in a form of lyophilized powder. The lyophilized powder can be prepared by conventional methods in the art.

The present invention also provides an injection solution obtained by reconstitution of the lyophilized powder, and can be directly used for injection.

A pharmaceutical formulation of the present invention can effectively suppress aggregation and deamidation of antibody, thereby prevent degradation of an antibody product, resulting in a stable injectable composition which can be stored for 6 months at 25° C. and stable for 12 months at 2-8° C. Moreover, a pharmaceutical composition of the present invention has a protective effect on the oxidative degradation of the protein, and can be compatible with glass and stainless steel containers and stably present in these containers.

A pharmaceutical formulation of the present invention is used for the prophylaxis or treatment of a PD-1 mediated diseases or disorders, wherein the disease or disorder is preferably cancer; more preferably a cancer expressing PD-L1; most preferably cancer selected from the group consisting of breast cancer, lung cancer, stomach cancer, intestinal cancer, kidney cancer, and melanoma; most preferably non-small cell lung cancer, melanoma and kidney cancer.

The use of the pharmaceutical formulation of the present invention, in the preparation of medicament for prophylaxis or treatment of a PD-1 mediated disease or disorder, wherein the disease or disorder is preferably cancer; more preferably a cancer expressing PD-L1; wherein the cancer is most preferably breast cancer, lung cancer, stomach cancer, intestinal cancer, kidney cancer, or melanoma; most preferably non-small cell lung cancer, melanoma or kidney cancer.

A method for preventing or treating a PD-1 mediated disease or disorder, wherein the disease or disorder is preferably cancer; more preferably a cancer expressing PD-L1; wherein the cancer is most preferably breast cancer, lung cancer, stomach cancer, intestinal cancer, kidney cancer, or melanoma; most preferably non-small cell lung cancer, melanoma or kidney cancer, wherein the method comprises administering to a subject in need thereof a pharmaceutical formulation of the present invention.

Terms

The present invention relates to a stable pharmaceutical liquid formulation, which can include a high concentration of an antibody against PD-1.

As used herein, "antibody" refers to immunoglobulin, a four-peptide chain structure formed by two identical heavy chains and two identical light chains connected together by disulfide bond.

The antibodies of the invention include murine antibody, chimeric antibody, humanized antibody, preferably humanized antibody.

The term "antigen-binding fragment" of an antibody (or simply "antibody fragment") refers to one or more fragments of an antibody that retain the ability to specifically bind to an antigen (e.g., PD-1). It has been shown that the antigen-binding function of an antibody can be realized by fragments of a full-length antibody. Antigen-binding portions can be produced by recombinant DNA techniques, or by enzymatic or chemical cleavage of intact immunoglobulins.

The term "CDR" refers to one of the six hypervariable regions within the variable domains of an antibody that mainly contribute to antigen binding. One of the most commonly used definitions for the six CDRs is provided by Kabat E. A. et al, (1991) Sequences of proteins of immunological interest. NIH Publication 91-3242). As used herein, Kabat definition of CDRs only applies to LCDR1, LCDR2 and LCDR3 of the light chain variable domain, as well as to HCDR1, HCDR2 and HCDR3 of the heavy chain variable domain.

In the present invention, an antibody light chain described herein comprises a light chain variable region and a light chain constant region, which can include a human or murine κ, λ chain or a variant thereof.

In the present invention, an antibody heavy chain described herein comprises a heavy chain variable region and a heavy chain constant region, which can include the heavy chain constant region of human or murine IgG1, IgG2, IgG3, IgG4 or a variant thereof.

The term "chimeric antibody", is an antibody which is formed by fusing the variable region of a murine antibody with the constant region of a human antibody, the chimeric antibody can alleviate the murine antibody-induced immune response. To establish a chimeric antibody, hybridoma secreting specific murine monoclonal antibody shall be established first, a variable region gene is cloned from the murine hybridoma, then a constant region gene of a desired human antibody is cloned according to the requirement, the murine variable region gene is connected to the human constant region gene to form a chimeric gene which can be inserted into an expression vector, and finally the chimeric antibody molecule is expressed in the eukaryotic or prokaryotic system.

The term "humanized antibody", also known as CDR-grafted antibody, refers to an antibody generated by murine CDR sequences grafted into human antibody variable region framework, comprising different types of sequences of human germline antibody framework. Humanized antibody avoids allogenic reaction induced by chimeric antibody which carries a large number of murine components. Such framework sequences can be obtained from public DNA database covering germline antibody gene sequences or obtained from published references.

The term "pharmaceutical formulation" refers to a preparations which is in such form as to permit the effective biological activity of the active ingredient, and contains no additional components which are toxic to a subject to which the formulation is administered.

The term "liquid" as used herein in connection with a formulation according to the invention denotes a formulation which is liquid at a temperature of at least about 2° C. to about 8° C. under atmospheric pressure.

The term "stabilizer" denotes a pharmaceutical acceptable excipient, which protects the active pharmaceutical ingredient and/or the formulation from chemical and/or physical degradation during manufacturing, storage and application. Chemical and physical degradation pathways of protein pharmaceuticals are reviewed by Cleland, J. L., M. F. Powell, et al. (1993). "The development of stable protein formulations: a close look at protein aggregation, deamidation, and oxidation." Crit Rev Ther Drug Carrier Syst 10(4): 307-77, Wang, W. (1999). "Instability, stabilization, and formulation of liquid protein pharmaceuticals." Int J Pharm 185(2): 129-88., Wang, W. (2000). "Lyophilization and development of solid protein pharmaceuticals." Int J Pharm 203(1-2): 1-60. and Chi, E. Y., S. Krishnan, et al. (2003). "Physical stability of proteins in aqueous solution: mechanism and driving forces in nonnative protein aggregation." Pharm Res 20(9): 1325-36. Stabilizers include, but are not limited to, saccharide, amino acids, polyols, surfactants, anti-oxidants, preservatives, cyclodextrines, polyethylenglycols (e.g. PEG 3000, 3350, 4000, 6000), albumin (e.g. human serum albumin (HSA), bovines serum albumin (BSA)), salts (e.g. sodium chloride, magnesium chloride, calcium chloride), chelators (e.g. EDTA) as hereafter defined. A stabilizer specifically used in embodiments of the present invention is selected from saccharides. More specifically, the stabilizer is selected from the group consisting of sucrose, trehalose, and sorbitol. The stabilizer can be present in the formulation in an amount from 30 mg/ml to 100 mg/ml, preferably from 60 mg/ml to 90 mg/ml. More specifically, sucrose or trehalose is used as a stabilizer in an amount of 90 mg/ml.

A "stable" formulation is one in which the protein therein, e.g. the antibody, essentially retains its physical and chemical stability, therefore its biological activity, upon storage.

A "stable liquid pharmaceutical antibody formulation" is a liquid antibody formulation with no significant changes observed at a refrigerated temperature (2-8° C.) for at least 12 months, particularly 2 years, and more particularly 3 years. The criteria for stability is the following: no more than 10%, particularly 5%, of antibody monomer is degraded as measured by size exclusion chromatography (SEC-HPLC). Furthermore, the solution is colorless or clear to slightly opalescent by visual analysis. The protein concentration of the formulation has a change no more than +/−10%. No more than 10%, particularly 5% of aggregation is formed. The stability is measured by methods known in the art such as UV spectroscopy, size exclusion chromatography (SEC-HPLC), Ion-Exchange Chromatography (IE-HPLC), turbidimetry and visual inspection.

The terms "Programmed Death 1," "Programmed Cell Death 1," "Protein PD-1," "PD-1," PDl," "PDCDl," "hPD-1" and "hPD-I" are used interchangeably, and include variants, isoforms, species homologs of human PD-1, and analogs having at least one common epitope with PD-1. A complete PD-1 sequence can be found under NCBI Reference Sequence: NM_005018.1.

The terms "anti-PD-1 antibody", "antibody against PD-1" and "anti-PD-1 antibody" refer to an antibody that is capable of binding to PD-1 with sufficient affinity such that the antibody is useful as a diagnostic and/or therapeutic agent in targeting PD-1. The term "binding to PD-1" as used herein means the binding of the antibody to PD-1 in either a BIAcore assay (Pharmacia Biosensor AB, Uppsala, Sweden) or in ELISA, in which purified PD-1 or PD-1 CHO transfectants are coated onto microtiter plates.

The concentration of the antibody against PD-1 comprised in a pharmaceutical formulation of the invention is in the range of 1 mg/ml to 60 mg/ml, particularly in the range of 20 mg/ml to 50 mg/ml, most particularly of 40 mg/ml.

The term "surfactant" as used herein denotes a pharmaceutically acceptable excipient which is used to protect protein formulations against mechanical stresses like agitation and shearing. Examples of pharmaceutically acceptable surfactants include polyoxyethylensorbitan fatty acid esters (Tween), polyoxy ethylene alkyl ethers (for example those commercially obtained under the trademark Brij™) and polyoxyethylene-polyoxypropylene copolymer (Poloxamer, Pluronic). Examples of polyoxyethylenesorbitan-fatty acid esters are polysorbate 20 (commercially obtained under the trademark Tween 20™) and polysorbate 80 (commercially obtained under the trademark Tween 80™).

The term "buffer" as used herein denotes a pharmaceutically acceptable excipient, which stabilizes the pH of a pharmaceutical formulation. Suitable buffers are well known in the art and can be found in the literature. Preferred pharmaceutically acceptable buffers include, but are not limited to, histidine-buffers, citrate-buffers, succinate-buffers, acetate-buffers, arginine-buffers, phosphate-buffers or mixtures thereof. Buffers of particular interest include a citrate-buffer or acetate-buffer with its pH adjusted with an acid or a base known in the art. The above mentioned buffers are generally used in an amount of about 1 mM to 50 mM, preferably about 10 mM to 30 mM, and more preferably about 10 mM. Independently from the buffer used, the pH can be adjusted to a value in the range from 4.5 to 6.0 and particularly to a value in the range from 4.8 to 5.6 and most particularly to pH 5.2 with an acid or a base known in the art, e.g. hydrochloric acid, acetic acid, phosphoric acid, sulfuric acid and citric acid, sodium hydroxide and potassium hydroxide.

In some embodiments, a stable anti-PD-1 antibody pharmaceutical formulation of the present invention comprises an antioxidant as a second stabilizer. An "antioxidant" is a pharmaceutically acceptable excipient, which prevents oxidation of the active pharmaceutical ingredient. Antioxidants include, but are not limited to, chelating agents such as EDTA, citric acid, ascorbic acid, bu-tylated hydroxytoluene (BHT), butylated hydroxy anisole (BHA), sodium sulfite, p-amino benzoic acid, glutathione, propyl gallate, cysteine, methionine, ethanol, benzyl alcohol and n-acetyl cysteine.

The term "saccharide" as used herein denotes a monosaccharide or an oligosaccharide. A monosaccharide is a monomeric carbohydrate which is not hydrolysable by acids, including a simple saccharide and its derivatives, e.g. aminosaccharide. Examples of monosaccharides include glucose, fructose, galactose, mannose, sorbose, ribose, deoxyribose, neuraminic acid. An oligosaccharide is a carbohydrate consisting of more than one monomeric saccharide unit connected via glycosidic bond(s), either branched or in a chain. The monomeric saccharide units within an oligosaccharide can be identical or different. Depending on the number of monomeric saccharide units, the oligosaccharide is a di-, tri-, tetra-penta-saccharide, and so forth. In contrast to polysaccharides, the monosaccharides and oligosaccharides are water soluble. Examples of oligosaccharides include sucrose, trehalose, lactose, maltose and raffmose. In particular, saccharides are selected from the group consisting of sucrose and trehalose.

The term "amino acid" as used herein denotes a pharmaceutically acceptable organic molecule possessing an amino moiety located at α-position of a carboxylic group. Examples of amino acids include arginine, glycine, ornithine, lysine, histidine, glutamic acid, asparaginic acid isoleucine, leucine, alanine, phenylalanine, tyrosine, tryptophane, methionine, serine, proline. Amino acids are generally used in an amount of about 5 to 500 mM, particularly in an amount of about 5 mM to about 200 mM, and more particularly in an amount of about 100 mM to about 150 mM.

The term "stabilizer" also includes lyoprotectants. The term "lyoprotectant" denotes a pharmaceutical acceptable excipient, which protects the labile active ingredient (e.g. a protein) against destabilizing conditions during the lyophilisation process, subsequent storage and reconstitution. Lyoprotectants include, but are not limited to, one selected from the group consisting of saccharides, polyols (such as e.g. sugar alcohols) and amino acids. In particular, lyoprotectants can be selected from the group consisting of saccharides such as sucrose, trehalose, lactose, glucose, mannose, maltose, galactose, fructose, sorbose, raffinose, neuraminic acid, aminosaccharides such as glucosamine, galactosamine, N-methylglucosamine ("Meglumine"), polyols such as mannitol and sorbitol, and amino acids such as arginine and glycine or mixtures thereof. The cryoprotectant is preferably a disaccharide. It was surprisingly found in the present invention that disaccharides exhibit better effect on the stability of formulations of the present invention than that of monosaccharides, polyols, and amino acids.

A pharmaceutical formulation of the invention can also contain tonicity agents. The term "tonicity agent" as used herein denotes pharmaceutically acceptable tonicity agents which are used to modulate the tonicity of the formulation. The formulation can be hypotonic, isotonic or hypertonic. Isotonicity in general relates to the relative osmotic pressure of a solution, usually relative to that of human serum. A formulation according to the invention can be hypotonic, isotonic or hypertonic, but will preferably be isotonic. An isotonic formulation is liquid or liquid reconstituted from a solid form (e.g. from a lyophilized form) and denotes a solution having the same tonicity as that of other solution with which it is compared, such as physiologic salt solution and the serum. Suitable tonicity agents include, but are not limited to, sodium chloride, potassium chloride, glycerin and any component selected from the group of consisting of amino acids, saccharides, in particular glucose. Tonicity agents are generally used in an amount of about 5 mM to about 500 mM. As for stabilizers and tonicity agents, there are groups of compounds which can serve as both stabilizer and tonicity agent at the same time. Examples of such compounds can be found in the groups of saccharides, amino acids, polyols, cyclodextrines, polyethyleneglycols and salts. An example of saccharide that can serve as both stabilizer and tonicity agent is trehalose.

A pharmaceutical formulation of the present invention can also contain adjuvants such as preservatives, wetting agents, emulsifying agents and dispersing agents. Prevention of presence of microorganisms can be ensured by both sterilization procedures and the inclusion of various antibacterial and antifungal agents, for example, paraben, chlorobutanol, phenol, sorbic acid, and the like. Preservatives are generally used in an amount of about 0.001% to about 2% (w/v). Preservatives include, but are not limited to, ethanol, benzyl alcohol, phenol, m-cresol, p-chlor-m-cresol, methyl or propyl parabens, benzalkonium chloride.

A stable anti-PD-1 antibody pharmaceutical formulation of the present invention can be used for the prophylaxis or treatment of a PD-1 mediated disease or disorder, wherein the disease or disorder is preferably cancer; more preferably PD-L1 expressing cancer; wherein the disease or disorder is most preferably breast cancer, lung cancer, stomach cancer, intestinal cancer, kidney cancer, melanoma; most preferably non-small cell lung cancer, melanoma and kidney cancer.

A stable anti-PD-1 antibody pharmaceutical formulation according to the invention can be administered by intravenous (i.v.), subcutaneous (s.c.) or any other parental, administration means such as those known in the pharmaceutical art.

In view of its high stability, a pharmaceutical formulation according to the invention can be administered intravenously without the need of an in-line filter and is thus much more convenient to handle than conventional formulations that need to be administered via an in-line filter. In-line filters such as Sterifix® have to be installed in the infusion line of i.v. medications to prevent any particles, air, or microorganisms that may be present in the i.v. solution or line. Particles of 5 to 20 microns and larger size have the capability of obstructing blood flow through pulmonary capillaries, which could lead to complications such as pulmonary embolism. Foreign particles can also cause phlebitis at the injection site and filters may help to reduce the incidence of phlebitis.

The stable formulations to be used for in vivo administration must be sterile. This is readily accomplished by filtration through sterile filtration membranes.

A stable anti-PD-1 antibody pharmaceutical formulation according to the invention can be prepared by methods known in the art, e.g. ultrafiltration-diafiltration, dialysis, addition and mixing, lyophilization, reconstitution, and combinations thereof. Examples on preparations of formulations according to the invention can be found hereinafter.

A stable anti-PD-1 antibody pharmaceutical formulation according to the invention can also be in a lyophilized form or in a liquid form reconstituted from the lyophilized form. The "lyophilized form" is manufactured by lyophilization method known in the art. The lyophilizate usually has a residual moisture content of about 0.1% to 5% (w/w) and is present as a powder or a physically stable cake. The "reconstituted form" can be obtained from the lyophilizate by a fast dissolution after addition of reconstitution medium. Suitable reconstitution media include, but are not limited to, water for injection (WFI), bacteriostatic water for injection (BWFI), sodium chloride solutions (e.g. 0.9% (w/v) NaCl), glucose solutions (e.g. 5% (w/v) glucose), surfactant-containing solutions (e.g. 0.01% (w/v) polysorbate 20) and pH-buffered solutions (e.g. phosphate-buffered solutions).

DETAILED DESCRIPTION OF THE INVENTION

Hereinafter, the present invention is further described in detail with reference to the following examples; however, these examples are for illustrative purposes only and are not intended to limit the scope of the invention.

In the examples of the present invention, where specific conditions are not described, the experiments are generally conducted under conventional conditions, or under conditions proposed by the material or product manufacturers. Where the source of the reagents is not specifically given, the reagents are commercially available conventional reagents.

EXAMPLES

The preparation process of the present invention is as follows:

Step 1: Samples of an anti PD-1 antibody stock solution were measured for the protein concentration of the antibody in an intermediate control measurement. After passing the intermediate control measurement, the anti PD-1 antibody stock solution was passed through a 0.22 μm PVDF filter and the filtrate was collected. The PD-1 antibody had the heavy chain amino acid sequence shown as SEQ ID NO: 7 and the light chain amino acid sequence shown as SEQ ID NO: 8. The antibody was prepared according to the method disclosed in WO2015/085847.

Step 2: the filtrate was filled in 20 ml vial to a fill volume of 5.3 ml with a half stopper, the loading volume variation was measured by sampling at the beginning, the middle and the end of the filling, respectively.

Step 3: The vial with a stopper containing the filtrate was loaded into the lyophilization chamber and lyophilized according to the following lyophilization process. After the lyophilization procedure was completed, the lyophilized powder was plugged in vacuum.

| Parameter | Temperature (° C.) | Time setting (min) | time of maintenance (min) | Vacuum degree (mbar) |
|---|---|---|---|---|
| Pre-frozen | −5 | 10 | 60 | / |
|  | −45 | 40 | 120 | / |
| First drying | −5 | 40 | 2100 | 0.1 |
| Second drying | 25 | 60 | 400 | 0.01 |

Step 4: with a capping machine, the vial containing the lyophilized powder was added an aluminum cover, and the cover was rolled.

Step 5: Visual inspection was performed to confirm there was no collapse of the product, discrepancy of the loading volume and other defects. The vial label was printed and pasted; the carton label was printed and the carton was folded, and the packing and labelling were performed.

The protein concentration was measured for the intermediate control by the ultraviolet spectrophotometer with the absorption peak at 280 nm (Thermo: Nanodrop 2000).

The 0.22 μm PVDF filter was Millipore Millipak-100.

Filling machine was Chutian technology KGS8/2-X2 linear filling machine.

Loading volume difference was detected using electronic balance weighing (manufacturer: Sartorius, model BSA423 S).

Tofflon Lyo-B (SIP.CIP) vacuum freeze dryer was used for lyophilization.

Shandong Penglai DZG-130 knife type automatic capping machine was used for capping machine.

Tianjin Jingtuo YB-2A clarity detector was used for visual inspection appearance.

The HPLC (SEC and IEC) measurements in the examples were performed using an Agilent 1200DAD High Pressure Liquid Chromatograph (TSK gel SuperSW mAb HR 300× 7.8 mm column and ProPac™ WCX-10 BioLC™, 250×4 mm column).

The thermal denaturation temperature (Tm) of the protein was measured using GE MicroCal VP-Capillary DSC differential scanning calorimeter.

The average particle size of DLS (Dynamic Light Scattering) was measured using a Malvern Zetasizer Nano ZS nano-particle size potentiometer.

Example 1

The anti-PD-1 antibody was formulated as a preparation at pH 4.8-5.6 containing 10 mM (sodium) acetate, 90 mg/mL α,α-trehalose dihydrate, 0.2 mg/mL polysorbate 20, respectively. The antibody protein concentration was 40 mg/mL. Each formulation was filtered and filled into a 20 mL neutral borosilicate glass syringe bottle at 5 mL/bottle for lyophilization, the glass bottle is sealed with a halogenated butyl rubber stopper which was used for injection and lyophilized sterile powder. The lyophilized product was stored at 25° C. and 40° C. for stability analysis. The results showed that the anti-PD-1 antibody was very stable at pH 4.8-5.6.

TABLE 1

The effect of pH on the degradation of anti-PD-1 antibody

| Test index | Storage conditions and time | pH 4.8 | pH 5.0 | pH 5.2 | pH 5.4 | pH 5.6 |
|---|---|---|---|---|---|---|
| SEC monomer (%) | 0 point | 98.0 | 97.9 | 97.9 | 97.9 | 97.9 |
| | 40° C., 35 Days | 97.3 | 97.5 | 97.6 | 97.6 | 97.4 |
| | 25° C., 30 Days | 97.6 | 97.7 | 97.8 | 97.8 | 97.8 |
| IEC main peak (%) | 0 point | 66.2 | 66.4 | 66.6 | 66.4 | 66.4 |
| | 40° C., 35 Days | 64.7 | 64.1 | 64.7 | 65.9 | 65.3 |
| | 25° C., 30 Days | 64.7 | 65.6 | 65.6 | 65.4 | 66.0 |

Example 2

In the following buffer solutions, anti-PD-1 antibody formulations with a protein concentration of 1 mg/ml were prepared.
1) Buffer 1: 10 mM (sodium) acetate, pH 5.0;
2) Buffer 2: 10 mM disodium hydrogen phosphate (citric acid), pH 5.0;
3) Buffer 3: 10 mM (sodium) succinate, pH 5.0
4) Buffer 4: 10 mM (sodium) citrate, pH 5.0

Figure 1:
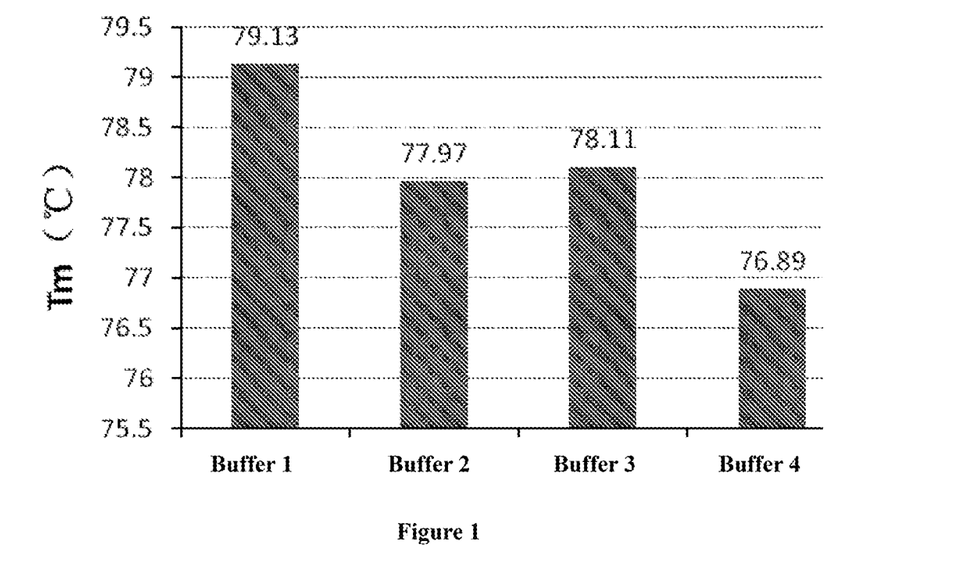
FIG. 1 shows the effect of the buffer system on the thermal stability of the anti-PD-1 antibody.

The thermal stability of anti PD-1 antibody in each formulation was measured by the differential scanning calorimetry (DSC). Analysis of the thermal denaturation median temperature (Tm) of the medicine showed that the stability of anti-PD-1 antibody in acetate buffer salt system was clearly better than that in succinate, citrate, disodium hydrogen phosphate buffer system. The result was shown in FIG. 1.

Example 3

The PD-1 antibody formulations comprising a protein concentration of 1 mg/mL and different saccharides of various concentrations were screened using DSC technology:
1) Buffer 1: 10 mM (sodium) acetate, 90 mg/mL sucrose, pH 5.2;
2) Buffer 2: 10 mM (sodium) acetate, 30 mg/mL α,α-trehalose dihydrate, pH 5.2;
3) Buffer 3: 10 mM (sodium) acetate, 60 mg/mL α,α-trehalose dihydrate, pH 5.2;
4) Buffer 4: 10 mM (sodium) acetate, 90 mg/mL α,α-trehalose dihydrate, pH 5.2.

Figure 2:
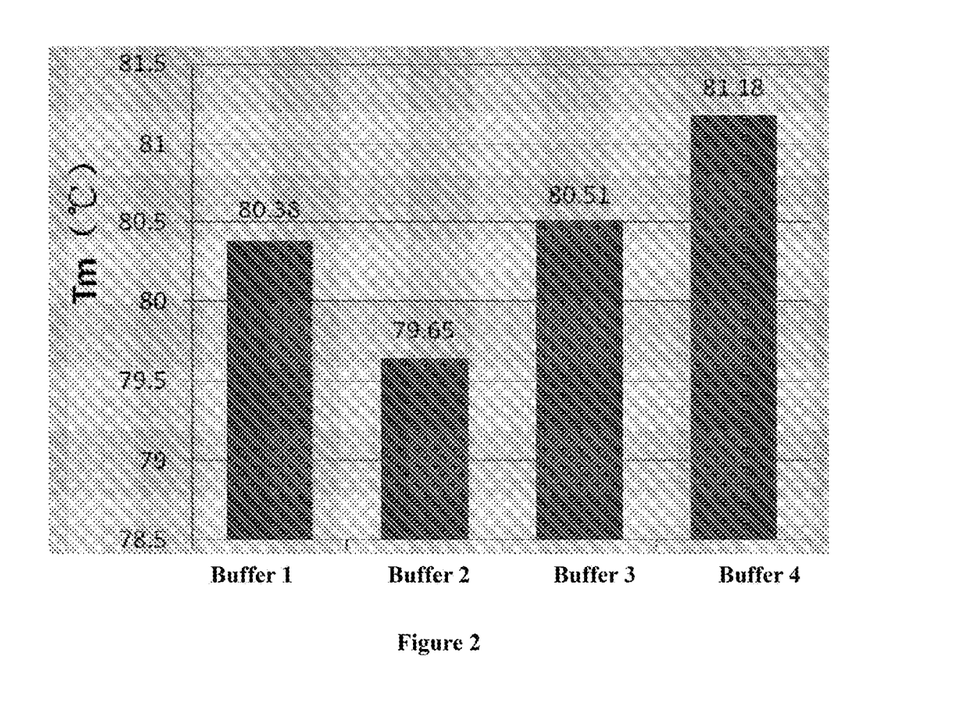
FIG. 2 shows the effect of saccharide on the thermal stability of the anti-PD-1 antibody.

Referring to FIG. 2, analysis of the Tm showed that the anti-PD-1 antibody had the best thermal stability when the concentration of α,α-trehalose dihydrate was 90 mg/mL.

Example 4

Anti-PD-1 antibody formulations comprising a PD-1 antibody protein concentration of 40 mg/mL, 10 mM (sodium) acetate, 90 mg/mL α,α-trehalose dihydrate and pH of 5.2 were prepared in the following buffer solutions which contained different concentrations of surfactant:
1) Without surfactant;
2) 0.1 mg/mL polysorbate 20;
3) 0.2 mg/mL polysorbate 20;
4) 0.3 mg/mL polysorbate 20;
5) 0.4 mg/mL polysorbate 20;
6) 0.2 mg/mL polysorbate 80;

Each formulation was filled in 20 mL vials with 5 mL/vial, and the vials were sealed with plastic film stopper. The drug was placed on a 25° C. thermostat shaker and shaken at 500 rpm. The results of stabilization showed that 0.1-0.4 mg/mL polysorbate 20 effectively prevented the anti-PD-1 antibody from aggregation and the formation of large particles.

TABLE 2

The effect of surfactant on the aggregation of anti-PD-1 antibodies at 25° C. and 500 rpm shaking

| Test Index | Shaking Time (hour) | 1 | 2 | 3 | 4 | 5 | 6 |
|---|---|---|---|---|---|---|---|
| Appearance | 0 | Clear | Clear | Clear | Clear | Clear | Clear |
| | 0.2 | Turbid | Clear | Clear | Clear | Clear | Clear |
| | 2 | N/A | Clear | Clear | Clear | Clear | Clear |
| | 6 | N/A | Clear | Clear | Clear | Clear | Clear |
| | 24 | N/A | Clear | Clear | Clear | Clear | Clear |
| DLS Average Diameter (nm) | 0 | 6.222 | 6.740 | 6.224 | 6.728 | 6.174 | 6.444 |
| | 0.2 | 8.102 | 7.725 | 6.384 | 6.642 | 6.598 | 6.574 |
| | 2 | N/A | 7.794 | 6.475 | 6.764 | 6.570 | 6.610 |
| | 6 | N/A | 7.435 | 6.286 | 6.710 | 6.280 | 6.750 |
| | 24 | N/A | 6.812 | 6.295 | 6.801 | 6.287 | 7.418 |
| SEC Monomer (%) | 0 | 97.9 | 98.3 | 97.9 | 98.1 | 97.9 | 98.0 |
| | 0.2 | 97.9 | 98.3 | 98.0 | 98.1 | 98.0 | 98.0 |
| | 2 | N/A | 98.2 | 98.0 | 98.1 | 98.0 | 98.0 |
| | 6 | N/A | 97.9 | 97.6 | 98.0 | 97.7 | 97.0 |
| | 24 | N/A | 97.3 | 97.6 | 97.9 | 97.7 | 96.3 |

Example 5

Anti-PD-1 antibody was prepared at 40 mg/mL in a solution comprising 10 mM (sodium) acetate, 90 mg/mL α,α-trehalose dihydrate, 0.2 mg/mL polysorbate 20 at pH 5.2. The formulation was filled in 20 mL vial with 5 mL/vial and lyophilized, and the vial was sealed with lyophilization stopper. The lyophilized samples were placed for 10 days under 4500±500 Lx light irradiation or placed for 10 days at 40±2° C., or subjected to a cycle of low temperature 4° C.~-40° C. for 3 times, or a cycle of freeze-thaw at -20° C.~-40° C. for 3 times. Drug stability was assessed by protein content, purity, and activity assay, and the results showed that the anti PD-1 antibody was stable in this prescription and could still meet the requirement even after the treatment of strong light, high temperature or low temperature and freeze-thaw cycles.

TABLE 3

Stability of anti PD-1 antibody formulations when exposed to strong light, high or low temperature and freeze-thaw cycles

| Test Index | Acceptable Limit | Null Point | Strong Light | High Temperature | Low Temperature Cycle | Freezing and thawing Cycle |
|---|---|---|---|---|---|---|
| Protein Content (mg/vial) | 200.0 ± 20.0 mg/vial | 195.4 | 197.5 | 201.0 | 197.5 | 190.5 |
| SEC Monomer (%) | ≥93.0% | 97.6 | 97.4 | 97.2 | 97.6 | 97.6 |
| IEC main peak (%) | ≥55.0% | 66.5 | 64.2 | 64.1 | 65.2 | 65.5 |
| Non-reducing CE-SDS main peak (%) | ≥90.0% | 95.6 | 95.8 | 95.7 | 94.9 | 95.1 |
| Reducing CE-SDS main peak (%) | ≥93.0% | 98.2 | 98.1 | 98.2 | 97.9 | 98.2 |
| Activity (%) | 70%~130% | 92 | 104 | 108 | 91 | 85 |

Example 6

Anti-PD-1 antibody was prepared at 40 mg/mL in a solution comprising 10 mM (sodium) acetate, 90 mg/mL α,α-trehalose dihydrate, 0.2 mg/mL polysorbate 20 at pH 5.2. The formulation was filled in glass bottles and 316L stainless steel tanks respectively, and placed for 24 hours at room temperature. Protein content and purity analysis showed that anti-PD-1 antibody was stable within 24 hours. The preparation was compatible with the 316L stainless steel tank.

TABLE 4

The stability of anti PD-1 antibody in stainless steel tank.

| Test Index | Quality Standard | storage Time (hour) | Glass | 316 L Stainless Steel Tank |
|---|---|---|---|---|
| Protein Concentration (mg/mL) | 40.0 ± 4.0 mg/mL | 0 | 39.4 | 39.4 |
| | | 3 | 39.2 | 39.0 |
| | | 6 | 38.9 | 39.0 |
| | | 24 | 39.3 | 38.7 |
| SEC Monomer (%) | ≥93.0% | 0 | 96.2 | 96.2 |
| | | 3 | 96.1 | 96.1 |
| | | 6 | 96.1 | 96.1 |
| | | 24 | 96.8 | 96.5 |
| IEC Main peak (%) | ≥55.0% | 0 | 68.2 | 68.2 |
| | | 3 | 68.1 | 68.0 |
| | | 6 | 68.3 | 68.5 |
| | | 24 | 68.0 | 67.5 |

Example 7

Anti-PD-1 antibody was prepared at 40 mg/mL in a solution comprising 10 mM (sodium) acetate, 90 mg/mL α,α-trehalose dihydrate, 0.2 mg/mL polysorbate 20 at pH 5.2. The formulation was filled into a 20 mL vial with 5 mL/vial and was lyophilized at primary drying temperature of -15° C., -10° C. and -5° C. respectively, and the vial was sealed with a lyophilization stopper. The lyophilized product was stored at 25° C. and its stability was analyzed. The results showed that the temperature at -10° C.~-5° C. was the best primary drying temperature for the lyophilization process.

TABLE 5

The stability of anti PD-1 antibody formulation prepared with different primary drying process.

| Primary drying temperature | Storage Time (Month) | SEC Monomer Purity (%) | DLS Average Diameter (nm) | Water Content (%) |
|---|---|---|---|---|
| -15° C. | 0 | 97.8 | 7.177 | 1.5 |
| | 1 | 97.9 | 7.172 | N/A |
| | 2 | 97.8 | 10.097 | N/A |
| -10° C. | 0 | 97.9 | 7.991 | 1.2 |
| | 1 | 97.9 | 7.318 | N/A |
| | 2 | 97.5 | 7.349 | N/A |
| -5° C. | 0 | 98.0 | 8.120 | 1.0 |
| | 1 | 97.6 | 7.781 | N/A |
| | 2 | 97.5 | 9.018 | N/A |

Example 8 Other Formulations

The present invention provides a stable pharmaceutical formulation comprising: a combination of an anti-PD-1 antibody (the heavy chain amino acid sequence of SEQ ID NO: 7 and the light chain amino acid sequence of SEQ ID NO: 8) and a stabilizing buffer selected from the following:
(i) 90 mg/mL α,α-trehalose dihydrate, and 10 mM acetate buffer at pH 5.2;
(ii) 90 mg/mL α,α-trehalose dihydrate, 0.2 mg/mL polysorbate 20, and 10 mM acetate buffer at pH 5.2;
(iii) 90 mg/mL α,α-trehalose dihydrate, 0.2 mg/mL polysorbate 20, and 20 mM acetate buffer at pH 5.4;
(iv) 60 mg/mL α,α-trehalose dihydrate, 0.4 mg/mL polysorbate 20, and 20 mM acetate buffer at pH 5.0;

(v) 60 mg/mL α,α-trehalose dihydrate, 0.1 mg/mL polysorbate 20, and 20 mM acetate buffer at pH 5.2;
(vi) 60 mg/mL α,α-trehalose dihydrate, 0.2 mg/mL polysorbate 20, and 10 mM acetate buffer at pH 5.2;
(vii) 30 mg/mL α,α-trehalose dihydrate, 0.4 mg/mL polysorbate 20, and 10 mM acetate buffer at pH 4.8;
(viii) 30 mg/mL α,α-trehalose dihydrate, 0.2 mg/mL polysorbate 20, and 30 mM acetate buffer at pH 5.2; or
(ix) 30 mg/mL α,α-trehalose dihydrate, 0.4 mg/mL polysorbate 20, and 10 mM acetate buffer at pH 5.6.

In the above examples, the concentration of anti-PD-1 antibody was from 1 mg/mL to 60 mg/mL, preferably 20-50 mg/mL, more preferably 35-45 mg/mL, and most preferably 40 mg/mL. The embodiment that can be performed can be selected from, but is not limit to, the following combinations:

(1) an anti PD-1 antibody 40 mg/mL, 90 mg/mL α,α-trehalose dihydrate, 0.2 mg/mL polysorbate 20, and 10 mM acetate buffer at pH 5.2;
(2) an anti PD-1 antibody 1 mg/mL, 30 mg/mL α,α-trehalose dihydrate, 0.2 mg/mL polysorbate 20, and 10 mM acetate buffer at pH 4.5;
(3) an anti PD-1 antibody 20 mg/mL, 60 mg/mL α,α-trehalose dihydrate, 0.2 mg/mL polysorbate 20, and 1 mM acetate buffer at pH 4.8;
(4) an anti PD-1 antibody 35 mg/mL, 85 mg/mL α,α-trehalose dihydrate, 0.2 mg/mL polysorbate 20, and 2 mM acetate buffer at pH 5.6;
(5) an anti PD-1 antibody 45 mg/mL, 95 mg/mL α,α-trehalose dihydrate, 0.2 mg/mL polysorbate 20, and 5 mM acetate buffer at pH 6.0;
(6) an anti PD-1 antibody 50 mg/mL, 100 mg/mL α,α-trehalose dihydrate, 0.2 mg/mL polysorbate 20, and 15 mM acetate buffer at pH 5.2;
(7) an anti PD-1 antibody 60 mg/mL, 90 mg/mL sucrose, 0.2 mg/mL polysorbate 400, and 30 mM acetate buffer at pH 5.2;
(8) an anti PD-1 antibody 40 mg/mL, 90 mg/mL lactose, 0.2 mg/mL polysorbate 60, and 50 mM acetate buffer at pH 4.5;
(9) an anti PD-1 antibody 40 mg/mL, 90 mg/mL trehalose, 0.2 mg/mL polysorbate 80, and 10 mM acetate buffer at pH 5.2;
(10) an anti PD-1 antibody 40 mg/mL, 90 mg/mL maltose, 0.2 mg/mL polyoxyethylene hydrogenated castor oil, and 10 mM acetate buffer at pH 5.2;
(11) an anti PD-1 antibody 40 mg/mL, 90 mg/mL α,α-trehalose dihydrate, 0.01 mg/mL glycerin fatty acid ester, and 10 mM acetate buffer at pH 5.2;
(12) an anti PD-1 antibody 40 mg/mL, 90 mg/mL α,α-trehalose dihydrate, 0.05 mg/mL polysorbate 20, and 10 mM acetate buffer at pH 5.2;
(13) an anti PD-1 antibody 40 mg/mL, 90 mg/mL α,α-trehalose dihydrate, 0.4 mg/mL polysorbate 20, and 10 mM acetate buffer at pH 5.2;
(14) an anti PD-1 antibody 40 mg/mL, 90 mg/mL α,α-trehalose dihydrate, 0.5 mg/mL polysorbate 20, and 10 mM acetate buffer at pH 5.2; and
(15) an anti PD-1 antibody 40 mg/mL, 90 mg/mL α,α-trehalose dihydrate, 1 mg/mL polysorbate 20, and 10 mM acetate buffer at pH 5.2.

The invention claimed is:

1. A pharmaceutical formulation, comprising an anti-PD-1 antibody, wherein the antibody comprises a heavy chain having the amino acid sequence of SEQ ID NO: 7, and a light chain having the amino acid sequence of SEQ ID: 8; and
  (i) 90 mg/ml α,α-trehalose dihydrate, and 10 mM acetate buffer at pH 5.2; or
  (ii) 90 mg/ml α,α-trehalose dihydrate, 0.2 mg/ml polysorbate 20, and 10 mM acetate buffer at pH 5.2; or
  (iii) 90 mg/ml α,α-trehalose dihydrate, 0.2 mg/ml polysorbate 20, and 20 mM acetate buffer at pH 5.4; or
  (iv) 60 mg/ml α,α-trehalose dihydrate, 0.4 mg/ml polysorbate 20, and 20 mM acetate buffer at pH 5.0; or
  (v) 60 mg/ml α,α-trehalose dihydrate, 0.1 mg/ml polysorbate 20, and 20 mM acetate buffer at pH 5.2; or
  (vi) 60 mg/ml α,α-trehalose dihydrate, 0.2 mg/ml polysorbate 20, and 10 mM acetate buffer at pH 5.2; or
  (vii) 30 mg/ml α,α-trehalose dihydrate, 0.4 mg/ml polysorbate 20, and 10 mM acetate buffer at pH 4.8; or
  (viii) 30 mg/ml α,α-trehalose dihydrate, 0.2 mg/ml polysorbate 20, and 30 mM acetate buffer at pH 5.2; or
  (ix) 30 mg/ml α,α-trehalose dihydrate, 0.4 mg/ml polysorbate 20, and 10 mM acetate buffer at pH 5.6.

2. The stable anti-PD-1 antibody pharmaceutical formulation according to claim 1, wherein the pharmaceutical formulation is an injectable pharmaceutical formulation which further comprises water for injection.

3. A lyophilized powder prepared from the pharmaceutical formulation according to claim 2.

4. The lyophilized powder according to claim 3, wherein an optimum drying temperature of −10° C. to −5° C. is used in lyophilization process.

5. An injection solution, obtained by dissolving the lyophilized powder according to claim 3.

6. A stable anti-PD-1 antibody pharmaceutical formulation comprising:
  (i) an anti-PD-1 antibody comprising a heavy chain having the amino acid sequence of SEQ ID NO: 7 and a light chain having the amino acid sequence of SEQ ID NO: 8;
  (ii) a buffer selected from the group consisting of an acetate buffer, a citrate buffer, a succinate buffer, and a phosphate buffer;
  (iii) a stabilizer selected from the group consisting of a saccharide and an amino acid, and
  (iv) a surfactant selected from the group consisting of polyoxyethylene hydrogenated castor oil, a glycerol fatty acid ester, and a polyoxyethylene sorbitan fatty acid ester.

7. The pharmaceutical formulation according to claim 6, wherein the concentration of the anti-PD-1 antibody is in the range of 1 mg/ml to 60 mg/ml.

8. The pharmaceutical formulation according to claim 7, wherein the concentration of the anti-PD-1 antibody is 40 mg/ml.

9. The stable anti-PD-1 antibody pharmaceutical formulation according to claim 6, wherein the pharmaceutical formulation is an injectable pharmaceutical formulation which further comprises water for injection.

10. A lyophilized powder prepared from the pharmaceutical formulation according to claim 6.

11. The lyophilized powder according to claim 10, wherein an optimum drying temperature of −10° C. to −5° C. is used in lyophilization process.

12. The pharmaceutical formulation according to claim 6, wherein the buffer is the acetate buffer.

13. The pharmaceutical formulation according to claim 12, wherein the concentration of the buffer is 1-50 mM.

14. The pharmaceutical formulation according to claim 6, wherein the pH of the formulation ranges from 4.5 to 6.0.

15. The pharmaceutical formulation according to claim 6, wherein the at least one stabilizer comprises a disaccharide selected from the group consisting of sucrose, lactose, trehalose, and maltose.

16. The pharmaceutical formulation according to claim 15, wherein the disaccharide is at a concentration from 30 mg/ml to 120 mg/ml.

17. The pharmaceutical formulation according to claim 6, wherein the surfactant is the polyoxyethylene sorbitan fatty acid ester selected from the group consisting of polysorbate 20, 40, 60 and 80.

18. The pharmaceutical formulation according to claim 17, wherein the surfactant is at a concentration from 0.01 mg/ml to 1 mg/ml.

\* \* \* \* \*

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial
<220> FEATURE:
<223> OTHER INFORMATION: PD-1 FORM HCDR1

<400> SEQUENCE: 1

Ser Tyr Met Met Ser
1               5

<210> SEQ ID NO 2
<211> LENGTH: 17
<212> TYPE: PRT
<213> ORGANISM: Artificial
<220> FEATURE:
<223> OTHER INFORMATION: PD-1 FORM HCDR2

<400> SEQUENCE: 2

Thr Ile Ser Gly Gly Gly Ala Asn Thr Tyr Tyr Pro Asp Ser Val Lys
1               5                   10                  15

Gly

<210> SEQ ID NO 3
<211> LENGTH: 7
<212> TYPE: PRT
<213> ORGANISM: Artificial
<220> FEATURE:
<223> OTHER INFORMATION: PD-1 FORM HCDR3

<400> SEQUENCE: 3
```

```
Gln Leu Tyr Tyr Phe Asp Tyr
1               5

<210> SEQ ID NO 4
<211> LENGTH: 11
<212> TYPE: PRT
<213> ORGANISM: Artificial
<220> FEATURE:
<223> OTHER INFORMATION: PD-1 FORM LCDR1

<400> SEQUENCE: 4

Leu Ala Ser Gln Thr Ile Gly Thr Trp Leu Thr
1               5                  10

<210> SEQ ID NO 5
<211> LENGTH: 7
<212> TYPE: PRT
<213> ORGANISM: Artificial
<220> FEATURE:
<223> OTHER INFORMATION: PD-1 FORM LCDR2

<400> SEQUENCE: 5

Thr Ala Thr Ser Leu Ala Asp
1               5

<210> SEQ ID NO 6
<211> LENGTH: 9
<212> TYPE: PRT
<213> ORGANISM: Artificial
<220> FEATURE:
<223> OTHER INFORMATION: PD-1 FORM LCDR3

<400> SEQUENCE: 6

Gln Gln Val Tyr Ser Ile Pro Trp Thr
1               5

<210> SEQ ID NO 7
<211> LENGTH: 443
<212> TYPE: PRT
<213> ORGANISM: Artificial
<220> FEATURE:
<223> OTHER INFORMATION: PD-1 FORM Heavy chain

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Met Met Ser Trp Val Arg Gln Ala Pro Gly Lys Gly Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
    195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
        260                 265                 270

Trp Tyr Val Asp Gly Val Glu Val His Asn Ala Lys Thr Lys Pro Arg
    275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
        420                 425                 430

Thr Gln Lys Ser Leu Ser Leu Ser Leu Gly Lys
    435                 440

<210> SEQ ID NO 8
<211> LENGTH: 214
<212> TYPE: PRT
<213> ORGANISM: Artificial
<220> FEATURE:
<223> OTHER INFORMATION: PD-1 FORM  Light chain

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Thr Trp Tyr Gln Gln Lys Pro Gly Lys Ala Pro Lys Leu Leu Ile
        35                  40                  45

Tyr Thr Ala Thr Ser Leu Ala Asp Gly Val Pro Ser Arg Phe Ser Gly
50                  55                  60
```

```
Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Val Tyr Ser Ile Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```